United States Patent [19]
Hanagata et al.

[11] Patent Number: 5,795,980
[45] Date of Patent: Aug. 18, 1998

[54] METHOD OF PREPARING GANGLIOSIDE

[75] Inventors: Goro Hanagata, Sayama; Susumu Miura, Kawagoe; Kiyoshi Tatsumi, Iruma, all of Japan

[73] Assignee: Snow Brand Milk Products Co., Ltd., Hokkaido, Japan

[21] Appl. No.: 789,325

[22] Filed: Jan. 23, 1997

Related U.S. Application Data

[63] Continuation-in-part of Ser. No. 535,834, Sep. 28, 1995, abandoned.

[30] Foreign Application Priority Data

Sep. 30, 1994 [JP] Japan .................................. 6-261966

[51] Int. Cl.$^6$ .......................... C08B 37/00; A61K 31/715
[52] U.S. Cl. .................................. 536/124; 536/53; 514/61
[58] Field of Search .......................... 536/53, 124; 514/61

[56] References Cited

FOREIGN PATENT DOCUMENTS 2662697 12/1991 France.
05-304955 11/1993 Japan.

OTHER PUBLICATIONS

Lagreid et al. *J. Chromatogr.* 1986, 377, 59–67.

*Primary Examiner*—Kathleen K. Fonda
*Attorney, Agent, or Firm*—Townsend&Banta

[57] ABSTRACT

A method of preparing Ganglioside $G_{M3}$ which comprises thermally treating a lipid containing material which includes Ganglioside $G_{D3}$ at a temperature of from 60° to 140° C., for a period of from 2 to 180 minutes at a pH ranging from 6–8. The lipid containing material contains at least 10 wt % liquid and is cream or a milk product prepared from cream.

18 Claims, 2 Drawing Sheets

A # METHOD OF PREPARING GANGLIOSIDE

This application is a continuation-in-part application of application Ser. No. 08/535,834, filed Sep. 28, 1995, now abandoned.

BACKGROUND OF THE INVENTION

1. Field of the Invention

The present invention relates to a method of preparing Ganglioside. In particular, the present invention relates to a method of preparing Ganglioside $G_{m3}$ from Ganglioside $G_{D3}$ included in a raw material containing lipids in situ.

The Ganglioside $G_{M3}$ prepared by the method of the present invention is useful as a material for the manufacture of pharmaceuticals, cosmetics, foods, beverages and animal feeds.

2. Description of the Prior Art

Ganglioside is a general name of sphingoglycolipid having sialic acid, and the existence of various molecular species thereof are known. Among them, Ganglioside $G_{M3}$ has a structure in which reducing terminal of lactose bonds to a ceramide and a sialic acid a 2–3 bonds to non-reducing terminal of the lactose. Ganglioside $G_{D3}$ has a structure in which a further sialic acid a 2–8 bonds to non-reducing terminal of Ganglioside $G_{M3}$, and thus the whole molecule of Ganglioside $G_{D3}$ has two molecules of sialic acid.

As for Ganglioside $G_{M3}$, various physiological functions have been known, and for example, proliferation inhibiting function of keratinocyte, angiogenic repressing function and differentiation function of leukocyte have been reported. In addition, Ganglioside $G_{M3}$ has been known to be a receptor to influenza or Newcastle disease viruses.

As a method of preparing Ganglioside $G_{M3}$ from Ganglioside $G_{D3}$, a method of hydrolyzing Ganglioside $G_{D3}$ with sialidase or a method of hydrolyzing Ganglioside $G_{D3}$ with an acid is known (Japanese Patent Application (OPI) No. 5-279379). However, the method of hydrolyzing with sialidase is not always considered to be an industrially advantageous method, since Ganglioside is inhibited by coexisting proteins, substrates are easily inhibited by coexisting free sialic acid and bonding sialic acid and the like, and the sialidase used is expensive. In addition, with the method of hydrolyzing with an acid, precipitates of proteins are easily produced although the cost needed for the conversion is low. It is, therefore, very difficult to apply this method to a raw material containing a high amount of proteins such as bovine milk or milk products. Further, there is a problem that viscosity of solution is easily increased when hydrolyzed with an acid.

It is known that Ganglioside exists in milk fat globule membrane, animal cells or animal brains, and that among them Ganglioside $G_{D3}$ exists in milk fat globule membrane in a high amount. The material containing a high amount of Ganglioside $G_{D3}$ generally contains a high amount of lipids such as triglyceride or phospholipid since the milk fat globule membrane is contained in milk products, in particular, in cream or processed cream products, in a high amount.

SUMMARY OF THE INVENTION

The present inventors have researched a method of preparing Ganglioside $G_{M3}$ from Ganglioside $G_{D3}$ to find out that Ganglioside $G_{D3}$ may be converted into Ganglioside $G_{M3}$ by thermally treating a raw material containing lipids including Ganglioside $G_{D3}$ at a neutral pH zone ranging from 6 to 8 to desialize only one sialic acid molecule bonded to non-reducing terminal of Ganglioside $G_{D3}$ without the need of the addition of an acid or an alkali, and thus completed the present invention.

Under such circumstances, an object of the present invention is to provide a method of preparing Ganglioside $G_{M3}$ by converting Ganglioside $G_{D3}$ included in a raw material containing lipids into Ganglioside $G_{M3}$ in situ by thermally treating the raw material at a neutral pH zone ranging from 6 to 8.

In accordance with the present invention, there is provided a method of preparing Ganglioside $G_{M3}$ which comprises converting Ganglioside $G_{D3}$ included in a raw material containing lipids into Ganglioside $G_{M3}$ in situ.

In accordance with the present invention, there is provided a method of preparing Ganglioside $G_{M3}$ wherein said conversion of Ganglioside $G_{D3}$ into Ganglioside $G_{M3}$ is carried out by thermally treating the raw material in a neutral condition.

In accordance with the present invention, there is provided a method of preparing Ganglioside $G_{M3}$ wherein the thermal treatment is carried out at a pH ranging from 6 to 8.

DETAILED DESCRIPTION OF THE PREFERRED EMBODIMENTS

Figure 1:
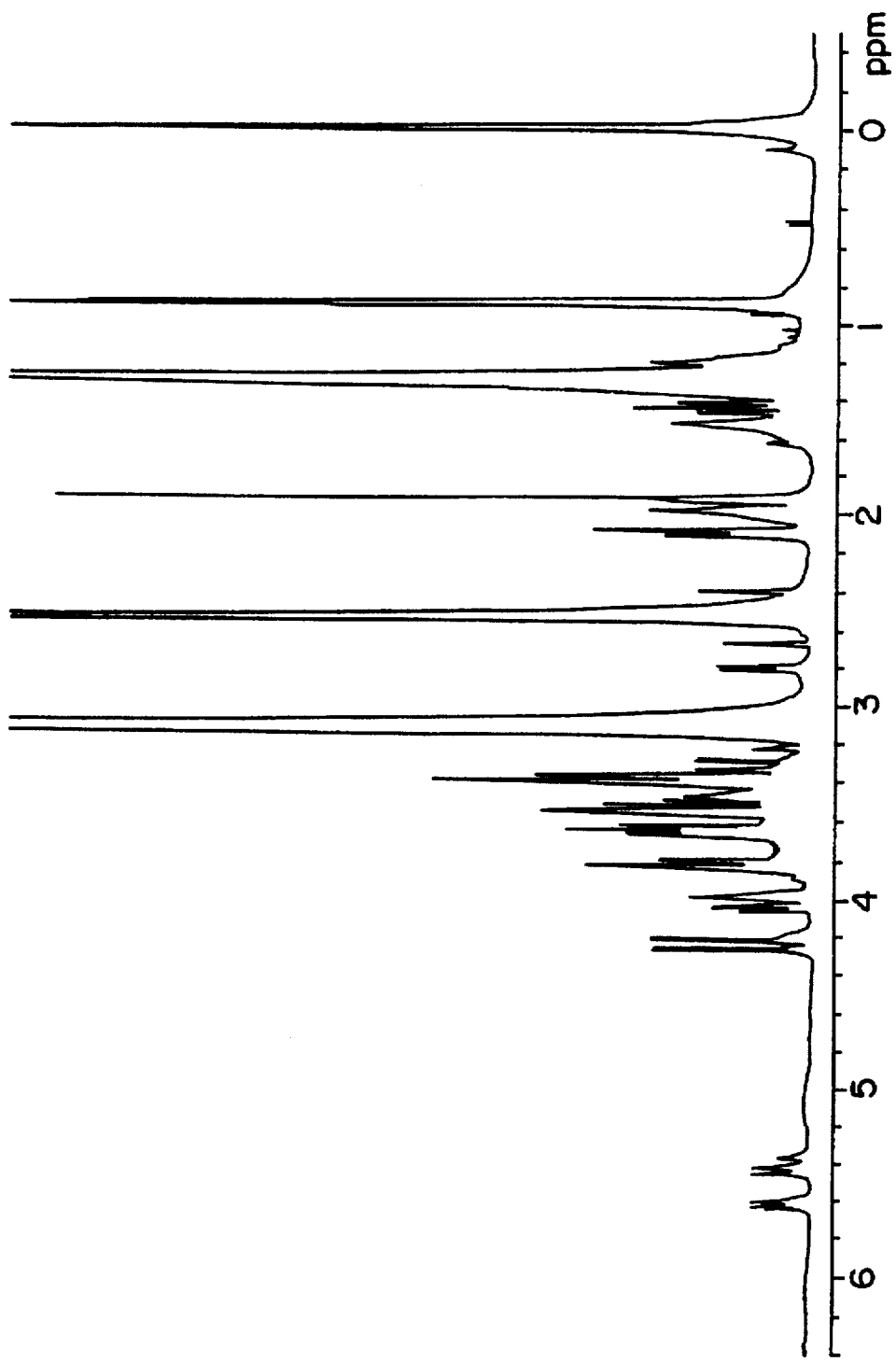
FIG. 1 shows an NMR spectrum of the reaction product obtained in EXAMPLE 1.

The features of the method of the present invention is to convert Ganglioside $G_{D3}$ included in a raw material containing lipids into Ganglioside $G_{M3}$ in situ. As the raw material containing lipids used in the present invention, a raw material containing 10 wt % or more lipids per solids is preferably used, e.g., cream or milk products prepared using cream as a raw material may be used. In addition, a raw material containing lipid including Ganglioside $G_{D3}$, obtained from fresh milk, cream, buttermilk, whey protein concentrates (WPC) or whey cream obtained by a method of extracting it from a raw material containing Ganglioside $G_{D3}$ with an organic solvent such as ethanol (Japanese Patent Application (OPI) No. 2-207090) may be used. The term lipids used herein means triglyceride, phospholipid, glycolipid or a material which may be extracted with a polar solvent such as chloroform-methanol mixture, and further means a fat soluble material such as carotenoid or sterol.

The thermal treatment is preferably carried out at a higher temperature than the temperatures usually adopted to heat foods or milk products. In the method of the present invention, by heating the raw material in a neutral pH zone preferably ranging from 6 to 8, only one molecule of sialic acid can be desialized from Ganglioside $G_{D3}$ to obtain Ganglioside $G_{M3}$. But if the heating is continued, the produced Ganglioside $G_{M3}$ will further be desialized to liberate the remaining sialic acid. The higher a reaction temperature, the higher a production rate of Ganglioside $G_{M3}$ becomes but the higher a decomposition rate of Ganglioside $G_{M3}$ becomes. Thus, a reaction temperature of the thermal treatment is set in the range of from 60° C. to 140° C., preferably in the range of from 85° C. to 120° C., more preferably in the range of from 85° C. to 95° C. The reaction temperature may be determined depending on the raw material used.

A reaction time of the thermal treatment may be determined depending on the temperature in order to obtain Ganglioside $G_{M3}$ in a high yield. The reaction time is set in the range of from 45 minutes to 180 minutes when the reaction temperature is in the range of from 60° C. to 95° C., and set in the range of from 2 minutes to 120 minutes when the temperature is from 95° C. to 140° C.

Preferably, the reaction time is set in the range of from 45 minutes to 160 minutes when the reaction temperature is in the range of from 85° C. to 95° C., and in the range of from 5 minutes to 120 minutes when the temperature is from 95° C. to 120° C.

Most preferably, the reaction temperature is in the range of from 85° C. to 95° C., and the reaction time is in the range of from 45 minutes to 160 minutes.

If the temperature is higher than the above temperatures, and the time is longer than the above periods, the produced Ganglioside $G_{M3}$ eventually decomposes.

The amount of heat obtained by the thermal treatment of the present invention is greater than that obtained by the usual heat sterilization of milk. In general, the UHT sterilization of milk is carried out at 120° C. to 150° C. for 0.4 sec. to 4 sec. The HTST sterilization of milk is carried out at 72° C. to 85° C. for 2 sec. to 15 sec. The LTLT sterilization of milk is carried out at 62° C. to 65° C. for 30 minutes.

The Ganglioside prepared by the method of the present invention can be used as a material for the manufacture of pharmaceuticals, cosmetics, foods, beverages and animal feeds as it is, i.e., in a form included in the raw material containing lipids, or after separating or purifying it by a conventional method.

The following examples are further illustrative of the present invention, and are not to be construed as limiting the scope thereof. Unless expressly indicated to be otherwise, all parts and percentages are by weight.

EXAMPLES

Test Example 1

The relation between heating temperature and heating time was tested under the following conditions.

Material containing high $G_{D3}$:
$G_{D3}$=5.1 wt %
$G_{M3}$=detection limit or less
Proteins=1 wt %

5% Aqueous solution (each 1 ml) was used:
$G_{D3}$ concentration=2.55 g/L
Results are shown in the following Table.

| Temp (°C.) | Time (min) | Molar Ratio | | |
|---|---|---|---|---|
| | | $G_{D3}$ | $G_{M3}$ | Others |
| 85 | 80 | 53 | 28 | 19 |
| | 90 | 49 | 31 | 20 |
| | 100 | 43 | 31 | 26 |
| | 110 | 38 | 31 | 31 |
| | 140 | 33 | 33 | 34 |
| | 160 | 28 | 31 | 41 |
| 95 | 30 | 66 | 29 | 5 |
| | 45 | 50 | 42 | 8 |
| | 60 | 43 | 46 | 11 |
| | 75 | 37 | 42 | 21 |
| | 90 | 30 | 37 | 33 |
| | 120 | 19 | 38 | 43 |
| 100 | 15 | 65 | 22 | 13 |
| | 30 | 52 | 37 | 11 |
| | 45 | 34 | 42 | 24 |
| | 60 | 22 | 41 | 37 |
| 120 | 5 | 45 | 35 | 20 |
| | 10 | 15 | 30 | 55 |

The other components are estimated to be lactosyl ceramide.

Example 1

2 L of 80% ethanol was added to 100 g of buttermilk powder, and the mixture was stirred at room temperature for 8 hours. Then, precipitates were removed by filtration. Water was added, and the mixture was repeatedly distilled under a reduced pressure at a low temperature to remove ethanol, finally obtaining 2 L of an aqueous solution which was used as a starting material. The aqueous solution contained 2.6 g/L of Ganglioside $G_{D3}$ and 0.16 g/L Ganglioside $G_{M3}$. The pH of the aqueous solution was 6.8.

The aqueous solution was heated to 95° C. for 60 minutes to carry out a reaction. After completing the reaction, the reaction mixture was followed by thin layer chromatography (No. 13749; obtained from Merck). The thin layer chromatography was developed using a solvent (chloroform:methanol:$H_2O$=60:35:8, by vol.) and was color developed with resorcinol. It was confirmed, as the results, that the reaction mixture contained 0.95 g/L of Ganglioside $G_{M3}$.

Figure 2:
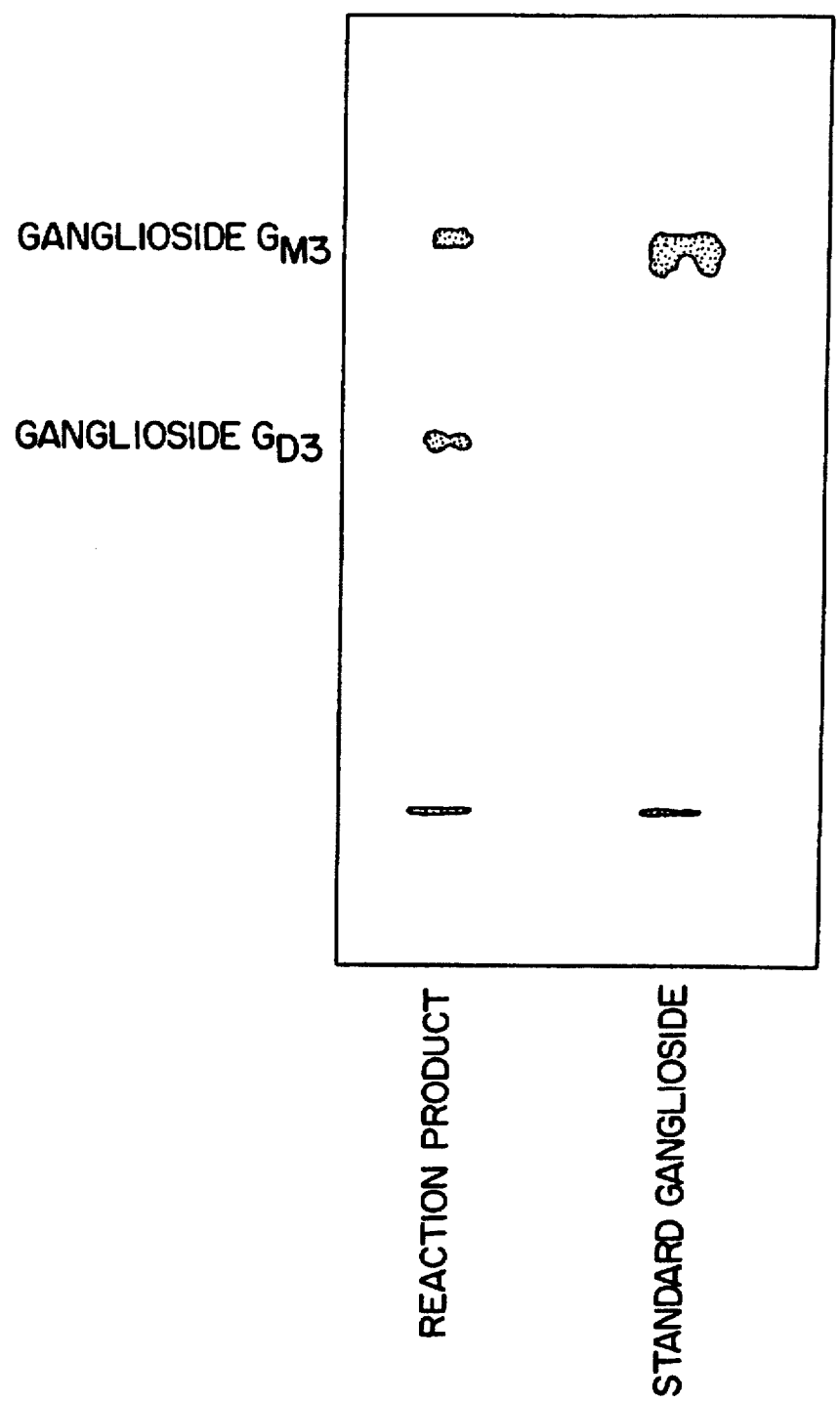
FIG. 2 shows a result of thin layer chromatography of the reaction product obtained in EXAMPLE 2.

The reaction mixture was dried under a reduced pressure to obtain white powder. The powder was followed by ion-exchange chromatography with DEAE-Sephadex A-25 (obtained from Pharmacia), and was followed by silica gel chromatography by Iatrobeads 6RS 8060 (obtained from Iatron Laboratories, Inc.) to collect a reaction product. After freeze drying the product, 0.90 g of the obtained white powder was analyzed with NMR to obtain a result as shown in FIG. 2. The result corresponded to the standard.

Example 2

2 L of cream containing 48 mg/L of Ganglioside $G_{D3}$ was heated to 85° C. for 60 minutes to carry out a reaction. After completing the reaction, a lipid fraction was extracted from the reaction mixture with-a solvent (chloroform:methanol= 2:1), and was followed by thin layer chromatography as described in EXAMPLE 1. The result was as shown in FIG. 2. It was proved that Ganglioside $G_{M3}$ has the same Rf values as the Ganglioside $G_{M3}$ derived from bovine brain. In addition, it was confirmed, by densitometry, that the reaction mixture contained 15 mg/L of Ganglioside $G_{M3}$.

By the method of the present invention, Ganglioside $G_{M3}$ can be prepared from Ganglioside $G_{D3}$ inexpensively and simply without the need of pH setting with an acid or an alkali. Thus, the method of the present invention is useful as an industrial method of preparing Ganglioside $G_{M3}$. In addition, since the Ganglioside $G_{M3}$ prepared by the method of the present invention has physiological functions such as infection protective ability, it is useful as a raw material for the manufacture of pharmaceuticals, cosmetics, foods, beverages and animal feeds.

The foregoing examples and description of the preferred embodiment should be taken as illustrating, rather than as limiting, the present invention as defined by the claims. As will be readily appreciated, numerous variations and combinations of the features set forth above can be utilized without departing from the present invention as set forth in the claims. Such variations are not regarded as a departure from the spirit and scope of the invention, and all such modifications are intended to be included within the scope of the following claims.

What is claimed is:

1. A method of preparing Ganglioside $G_{M3}$ which consists essentially of thermally treating a lipid containing material which includes Ganglioside $G_{D3}$ at a temperature of from 60° to 140° C., for a period of from 45 to 180 minutes when the temperature is from 60° C. to 95° C., or for a period of from 2 minutes to 120 minutes when the temperature is from 95° C. to 140° C.

2. The method of preparing Ganglioside $G_{M3}$ as in claim 1, wherein the Ganglioside $G_{D3}$ included in said lipid containing material is converted to Ganglioside $G_{M3}$ by thermally treating the lipid containing material at a neutral pH.

3. The method of preparing Ganglioside $G_{M3}$ as claimed in claim 1, wherein the thermal treatment is carried out at a temperature of from 85° to 120° C., for a period of from 45 to 160 minutes, when the temperature is from 85° C. to 95° C., or for a period of from 5 minutes to 120 minutes when the temperature is from 95° C. to 120° C.

4. The method of preparing Ganglioside $G_{M3}$ as in claim 3, wherein the thermal treatment is carried out at a temperature of from 85° to 95° C. for a period of from 45 to 160 minutes.

5. The method of preparing Ganglioside $G_{M3}$ as in claim 1, wherein said lipid containing material contains lipids to the extent of about at least 10% by weight.

6. The method of preparing Ganglioside $G_{M3}$ as in claim 1, wherein the lipid containing material is cream or a milk product prepared from cream.

7. An non-enzymatic method of preparing Ganglioside $G_{M3}$ from cream or a milk product prepared using cream consisting essentially of thermally treating cream or a milk product prepared using cream at a temperature of from about 60° to 140° C., for a period of from 45 to 180 minutes when the temperature is from 60° C. to 95° C., or for a period of from 2 minutes to 120 minutes when the temperature is from 95° to 140° C.

8. The non-enzymatic method as in claim 7, wherein the thermal treatment is carried out at a neutral pH.

9. The non-enzymatic method as in claim 8, wherein the thermal treatment is carried out at a pH of from 6 to 8.

10. The non-enzymatic method as in claim 7, wherein the thermal treatment is carried out at a temperature of from 85° to 120° C. for a period of from 45 to 160 minutes when the temperature is from 85° C. to 95° C., or for a period of from 5 minutes to 120 minutes when the temperature is from 95° C. to 120° C.

11. The non-enzymatic method as in claim 10, wherein the thermal treatment is carried out at a temperature of from 85° to 95° C., for a period of from 45 to 160 minutes.

12. The non-enzymatic method as in claim 7, wherein the cream or milk product prepared using cream contains lipids to the extent of at least 10% by weight.

13. The non-enzymatic method of preparing Ganglioside $G_{M3}$ from lipid containing material which includes Ganglioside $G_{D3}$ obtained from a material selected from the group consisting of fresh milk, cream, buttermilk, whey, protein concentrates and whey cream obtained by a method of extracting it from a raw material containing Ganglioside $G_{D3}$ with an organic solvent, said method consisting essentially of thermally treating at a temperature of from 60° to 140° C. said lipid containing material, for a period of from 45 to 180 minutes when the temperature is from 60° to 95° C., or for a period of from 2 to 120 minutes when the temperature is from 95° to 140° C.

14. The non-enzymatic method as in claim 13, wherein the thermal treatment is carried out at a neutral pH.

15. The non-enzymatic method as in claim 14, wherein the thermal treatment is carried out at a pH of from 6 to 8.

16. The non-enzymatic method as in claim 13, wherein the thermal treatment is carried out at a temperature of from about 85° to 120° C., for a period of from 45 to 160 minutes when the temperature is from 85° to 95° C., or for a period of from 5 minutes to 120 minutes when the temperature is from 95° C. to 120° C.

17. The non-enzymatic method as in claim 16, wherein the thermal treatment is carried out at a temperature of from about 85° to 95° C., for a period of from 45 to 160 minutes.

18. The non-enzymatic method as in claim 13, wherein the id containing material contains lipids to the extent of at least 10% by weight.

* * * * *